United States Patent
Taniguchi et al.

(10) Patent No.: US 8,339,136 B2
(45) Date of Patent: Dec. 25, 2012

(54) MAGNETIC RESONANCE IMAGING APPARATUS

(75) Inventors: Yo Taniguchi, Kokubunji (JP); Shinji Kurokawa, Kashiwa (JP); Suguru Yokosawa, Kokubunji (JP); Yoshitaka Bito, Kokubunji (JP)

(73) Assignee: Hitachi Medical Corporation, Tokyo (JP)

( * ) Notice: Subject to any disclaimer, the term of this patent is extended or adjusted under 35 U.S.C. 154(b) by 637 days.

(21) Appl. No.: 12/599,534

(22) PCT Filed: Apr. 28, 2008

(86) PCT No.: PCT/JP2008/058211
§ 371 (c)(1),
(2), (4) Date: Nov. 10, 2009

(87) PCT Pub. No.: WO2008/139925
PCT Pub. Date: Nov. 20, 2008

(65) Prior Publication Data
US 2010/0272336 A1    Oct. 28, 2010

(30) Foreign Application Priority Data
May 11, 2007   (JP) .................................. 2007-126549

(51) Int. Cl.
*G01V 3/00* (2006.01)
(52) U.S. Cl. .......................... 324/309; 324/306; 324/307
(58) Field of Classification Search .......... 324/306–309; 382/131
See application file for complete search history.

(56) References Cited

U.S. PATENT DOCUMENTS

| | | | | |
|---|---|---|---|---|
| 5,382,902 A | * | 1/1995 | Taniguchi et al. | 324/309 |
| 2003/0060698 A1 | * | 3/2003 | Mistretta | 600/410 |
| 2003/0130574 A1 | * | 7/2003 | Stoyle | 600/410 |
| 2004/0114791 A1 | * | 6/2004 | Atkinson | 382/131 |
| 2004/0140804 A1 | * | 7/2004 | Polzin et al. | 324/309 |
| 2009/0010514 A1 | * | 1/2009 | Kimura | 382/131 |
| 2010/0219828 A1 | * | 9/2010 | Takahashi et al. | 324/309 |

FOREIGN PATENT DOCUMENTS

JP   2006-223869   8/2006

OTHER PUBLICATIONS

David G. Kruger et al.; Continuously Moving Table Data Acquisition Method for Long FOV Contrast-Enhanced MRA and Whole-Body MRI; Magnetic Resonance in Medicine, Wiley-Liss, Inc. 2002, pp. 224-231; 47, Department of Radiology, Mayo Clinic, Rochester, MN 55905. E-mail: kruger.david@mayo.edu.

Jason A. Polzin et al.; Correction for Gradient Nonlinearity in Continuously Moving Table MR Imaging; Magnetic Resonance in Medicine, Wiley-Liss, Inc. 2004, pp. 181-187, 52; www.interscience.wiley.com.

* cited by examiner

*Primary Examiner* — Alexander H Taningco
(74) *Attorney, Agent, or Firm* — Antonelli, Terry, Stout & Kraus, LLP.

(57) ABSTRACT

In the continuous moving table imaging, an image is reconstructed with suppressed artifacts even in imaging under inhomogeneity of static magnetic field.

In a magnetic resonance imaging apparatus, signals are measured with moving a table to obtain multiple data sets, and inverse Fourier transform of each data set is carried out in the read-out direction to obtain hybrid data. One-dimensional data are extracted from each hybrid data at a border with respect to the adjacent hybrid data, and correction values for corrections of discontinuity of signal intensity and phase at a border of hybrid data are obtained by using the one-dimensional data. Data obtained by inverse Fourier transform of each hybrid data are corrected by using the correction values, and an image showing continuity for signal intensity and phase is eventually obtained.

11 Claims, 11 Drawing Sheets

MAGNETIC RESONANCE IMAGING APPARATUS

TECHNICAL FIELD

The present invention relates to a magnetic resonance imaging apparatus, and it especially relates to a technique for performing imaging while moving a table on which a subject is placed.

BACKGROUND ART

Magnetic resonance imaging (MRI) apparatuses are diagnostic imaging apparatuses for medical use with which a radio frequency magnetic field and a gradient magnetic field are applied to a subject placed in a static magnetic field, and echo signals generated by nuclear magnetic resonance from the subject are measured to reconstruct images. In such MRI apparatuses, the region in which the static magnetic field is uniform is a spherical region having a diameter of about 45 cm, and therefore the size of the region for which imaging can be attained by one time of measurement is usually limited to about 40 cm. Accordingly, when imaging is performed for a larger region such as the whole body, moving table imaging is performed in which imaging is performed with moving a bed (table) along the body axis direction of the subject. Types of such moving table imaging are roughly classified into two categories, i.e., those of multi-station imaging and continuous moving table imaging.

The multi-station imaging is a technique of forming a whole body image by dividing the whole body into multiple regions (stations), performing imaging of the stations and synthesizing images of the stations to create the whole body image. Since imaging for each station is performed with a fixed table, conventional imaging techniques can be used as they are. Moreover, the adjustment parameters which must be set according to imaging object such as resonance frequency, optimal irradiation intensity of the radio frequency magnetic field and gain of receiver coil can be obtained before the start of imaging of each station, like the conventional imaging. Thus, the multi-station imaging to which conventional imaging techniques can be applied as they are has already been clinically used.

On the other hand, continuous moving table imaging is a method of imaging with continuously moving the table (for example, Non-patent documents 1, 2 etc.). This method provides better imaging time efficiency compared with the multi-station imaging, since this method does not suffer from the time loss accompanying the movement of table. However, since the imaging should be performed while the subject is moving, conventional imaging techniques and image reconstruction techniques, as they are, are often inapplicable, and it has various problems to be solved for clinical application thereof.

Non-patent document 1: Kruger D G, Riederer S J, Grimm R C, Rossman P J, Continuously moving table data acquisition method for long FOV contrast-enhanced MRA and whole-body MRI, Magn. Reson. Med. 2002, 47:224-231

Non-patent document 2: Polzin J A, Kruger D G, Gurr D H, Brittain J H, Riederer S J, Correction for Gradient Nonlinearity in Continuously Moving Table MR Imaging, Magn. Reson. Med., 2004, 52:181-187

DISCLOSURE OF THE INVENTION

Object to be Achieved by the Invention

The reasons why the continuous moving table imaging is not clinically used include degradation of image quality due to apparatus distortion such as inhomogeneity of static magnetic field and nonlinearity of gradient magnetic field. In the continuous moving table imaging, the relative positions of the apparatus and the object of the imaging change for every signal measurement, and therefore influence of apparatus distortion such as inhomogeneity of static magnetic field and nonlinearity of gradient magnetic field does not come to be constant for every signal, unlike static imaging performed with a stationary table. Moreover, homogeneity of the static magnetic field is also influenced by magnetic susceptibility distribution, which substantially depends on the shape of the object of imaging, in addition to performance of magnet. Therefore, in the continuous moving table imaging, in which the object of imaging moves every moment during the imaging, it is difficult to always maintain homogeneity of the static magnetic field to be high. Accordingly, unless correction different from that of static imaging is performed, artifacts are generated in images.

For the nonlinearity of gradient magnetic field, a correction method using a map prepared by preliminary measurement has been proposed (refer to, for example, Non-patent document 2). As for the inhomogeneity of static magnetic field, it is conceivable to, for example, obtain optimal shimming information for arbitrary positions of the whole body beforehand before the start of imaging, and timely change the shimming information during the imaging with moving the table. However, in such a case, it takes time to obtain shimming information, which results in marked prolongation of imaging time, and therefore the advantage of the continuous moving table imaging, namely, superior imaging time efficiency, is impaired.

Therefore, an object of the present invention is to reconstruct an image with suppressed artifacts in the continuous moving table imaging performed in an MRI apparatus without extending imaging time, even if the imaging is performed in an inhomogeneous static magnetic field.

Means for Achieving the Object

In the magnetic resonance imaging apparatus of the present invention, signals are measured while moving a table to obtain multiple data sets, and the signals are corrected so that the data sets should have continuity for signal intensity and phase.

Specifically, the magnetic resonance imaging apparatus of the present invention comprises a table on which a subject is placed, a static magnetic field application part which applies a static magnetic field to the subject, a gradient magnetic field application part which applies a gradient magnetic field to the subject, an RF signal transmission and reception part which transmits and receives RF signals to and from the subject, a table driving part which moves the table relatively to the static magnetic field application part, a data processing part which creates image data from RF signals received by the RF signal transmission and reception part, and a control part which controls operations of the gradient magnetic field application part, the RF signal transmission and reception part, and the table driving part, and is characterized in that the control part controls the parts so that an operation of applying the gradient magnetic field to perform one cycle of phase encoding of a predetermined range while the table is relatively moved by the table driving part and thereby obtain a data set consisting of multiple RF signals should be repeated multiple times, and the data processing part comprises a hybrid data generation part which performs one-dimensional inverse Fourier transform of the data set obtained in each of the operations of multiple times in the read-out direction and thereby convert it into a hybrid data set, a correction part which performs correction for signal intensity continuity and phase continuity at borders of the multiple hybrid data sets generated by the hybrid data generation part, and an image generation part which synthesize hybrid data corrected by the correcting part and then performs one-dimensional inverse Fourier transform of the data in the direction of phase encoding.

For example, the correction part extracts one-dimensional data aligned along a border between adjacent hybrid data sets from a border region of one of the hybrid data sets, calculates a correction value used for the correction operation, for example, a phase value for correction for phase continuity (first correction value) and a phase value for correction for intensity continuity (second correction value), from the one-dimensional data, and corrects data of one of the hybrid data sets by using such a correction value. When three or more hybrid data sets are corrected, for example, one hybrid data set is used as a reference, and the other hybrid data sets are corrected so that they should conform with the reference.

Effect of the Invention

According to the present invention, in the continuous moving table imaging, discontinuity of data sets, each of which is obtained during one cycle of phase encoding, is eliminated, and thereby an image can be reconstructed with suppressed artifacts even in imaging under inhomogeneity of static magnetic field.

BEST MODE FOR CARRYING OUT THE INVENTION

Hereafter, embodiments of the present invention will be explained in detail with reference to the drawings.

First, an MRI apparatus to which the present invention is applied will be explained. FIG. 1 is a block diagram showing general configuration of an MRI apparatus 100. This MRI apparatus 100 comprises a magnet 101 which generates a static magnetic field, a coil 102 which generates magnetic field gradient in the space of the static magnetic field generated by the magnet 101, a gradient magnetic field power supply 105 for driving the coil 102, a probe 107 which irradiates a radio frequency magnetic field and detects nuclear magnetic resonance signals, a radio frequency magnetic field generator 106 and a receiver 108, which are connected to the probe 107, a table 152 on which a subject (e.g., living body) 103 is placed, a table movement control part 150, a sequencer 104 which controls operations of the aforementioned radio frequency magnetic field generator 106, receiver 108 and table movement control part 150, a computer 109 which is connected to the sequencer 104 and functions as a control system and a signal processing system, a display 110, a storage medium 111, and so forth.

The magnet 101 may be a superconducting magnet, a resistive magnet, a permanent magnet, or the like, and generates a vertical magnetic field or a horizontal magnetic field depending on the disposition scheme thereof. The subject 103 is placed on the table 152 in the space of the static magnetic field generated by the magnet 101. Movement of the table 152 is controlled by the table movement control part 150 according to directions of the sequencer 104. According to this embodiment, the table 152 moves in the direction of the body axis of the subject 103 (arrow 153) as shown in FIG. 2.

The sequencer 104 sends commands to the gradient magnetic field power supply 105 and the radio frequency magnetic field generator 106 to generate a gradient magnetic field and a radio frequency magnetic field, respectively. The radio frequency magnetic field is applied to the subject 103 via the probe 107. The nuclear magnetic resonance signals (henceforth referred to simply as echoes or echo signals) generated by the subject 103 are received by the probe 107 and detected by the receiver 108.

The computer 109 controls operations of the elements of the MRI apparatus 100 according to programs defined beforehand. Among the programs, a program describing generation timings and intensities of the radio frequency magnetic field and the gradient magnetic field, and signal reception timings to be controlled by the sequencer 104 is called a pulse sequence. The pulse sequence executed in this embodiment is not particularly limited so long as a sequence usable in continuous moving table imaging is chosen, and examples include SE type pulse sequences such as those for spin echo (SE) method and fast spin echo method, gradient echo (GrE) type pulse sequences, those for echo planar spectroscopic imaging (EPSI), and so forth. The sequencer 104 controls movement of the table 152 via the table movement control part 150 in a pulse sequence-synchronized manner.

The computer 109 receives the echo signals detected by the receiver 108, performs signal processing including A/D conversion, correction and image reconstruction such as inverse Fourier transform, and displays results on the display 110. The detected echo signals and measurement conditions are stored in the storage medium 111 as required. The details of the signal processing part in the computer 109 are shown in FIG. 3.

As shown in the drawing, in this embodiment, the signal processing part comprises, as functional parts, a hybrid data generation part 301 which performs one-dimensional inverse Fourier transform for each data set comprising multiple echo signals in the phase encoding direction and thereby generates hybrid data, a correction part 302 which performs correction of discontinuity of hybrid data, a synthesis part 303 which synthesizes the corrected hybrid data, and an image reconstruction part 304 which performs one-dimensional inverse Fourier transform of the synthesized hybrid data in the readout direction and create image data of the total region for which imaging is performed. The MRI apparatus according to this embodiment is characterized in that the signal processing part comprises the correction part 302 which performs correction of discontinuity of hybrid data, and the correction operation performed by this correction part 302 will be explained in detail later. Data obtained by inverse Fourier transform of the data of the kx-kz space, where the measured echoes are arranged, in the read-out direction (kz direction) are called hybrid data, and data obtained by inverse Fourier transform of the hybrid data in the direction of phase encoding (kx direction) are called real space data.

The operation of the MRI apparatus of this embodiment will be explained below. The flow of the operation is shown in FIG. 4.

First, in the continuous moving table imaging, a pulse sequence is repeatedly executed according to commands sent from the sequencer 104 with moving the table 152 in the direction of body axis of the subject 103 (arrow 153) as shown in FIG. 2 to perform imaging of a wide region of the subject 154 (this is called total FOV (field of view)) (Step 401). In this embodiment, provided that the moving direction of the table is the z-axis direction, an x-axis is defined in a direction perpendicular to the z-axis in a plane parallel to the table 152, and a y-axis is defined in a direction perpendicular to the z-axis and the x-axis, a reading gradient magnetic field shall be applied in the z-axis direction, and a phase encoding gradient magnetic field shall be applied to the x-axis direction.

The pulse sequence is executed at intervals of the repetition time Tr while changing the value of phase encoding kx by a certain constant value for every repetition to obtain one set of echoes (data set) for one cycle of the phase encoding. Since the positions of the table at the time of obtaining the echoes of this one set of echoes are different, they are different from data for one station such as those obtained in the multi-station imaging. However, they are called station data or data of subFOV here for convenience.

Then, inverse Fourier transform of the station data is carried out in the kz direction (read-out encoding direction) (Step 402). The data obtained by inverse Fourier transform of the echoes in the direction of phase encoding represents a projection image on the z-axis of imaging object, which has been phase-encoded in the x-axis direction in the subFOV, and is arranged in a kx-z space (hybrid space) constituted by a kx axis (phase encoding axis) as the vertical axis and a z-axis as the horizontal axis as shown in FIG. 5. Hybrid data (Hb data 501, hybrid data set) of each station obtained for each cycle of the phase encoding are arranged in a hybrid space according to the information of table positions recorded at the time of the measurement, and eventually constitutes Hb data of total FOV.

In the Hb data of each station, position of j-th (j=1, . . . ) echo in the z-axis direction, Zj, is represented as $Z1+(j-1)\times V\times Tr$, wherein Z1 is the position of the first echo, and V is the speed of the table. Further, provided that number of echo signals constituting data of subFOV is represented as nx, and size of total FOV in the direction of z is represented as Wz, the condition of $nx\times Tr\times V<Wz$ must be satisfied in order to thoroughly measure the kx-z space.

Even if the number of echoes nx, the table movement speed V, and the repetition time Tr are determined so that the kx-z space can be thoroughly measured, discontinuity is caused between the adjacent station Hb data 502 due to inhomogeneity of static magnetic field etc. When image data of total FOV are obtained by inverse Fourier transform of the Hb data of total FOV having discontinuity in the kx direction, artifacts are generated between the images of subFOV. In this embodiment, in order not to generate such artifacts, a correction operation which eliminates discontinuity between station Hb data is performed in the correction part 303 (Step 403), and then inverse Fourier transform of the Hb data is carried out in the kx direction to obtain image data of total FOV (Step 404). The correction for discontinuity may be such correction that continuity of echoes can be attained for both phase and intensity of the echoes. Hereafter, embodiments of the correction of discontinuity will be explained.

<First Embodiment>

In the first embodiment of the correction operation, correction for phase continuity at borders of station Hb data and correction for intensity continuity at borders of hybrid data are performed stepwise. The details of the correction operation shown in FIG. 4 (Step 403) are shown in FIG. 6.

First, correction is performed so that connection at each border of station Hb data (FIG. 5, 502) should become smooth with regard to intensity (Step 610). This correction will be explained with reference to FIGS. 7 and 8. FIG. 7, (a) and (b) show two of adjacent station Hb data m(i) and m(i+1) (i= 1, . . . ) before and after the correction by Step 610. In the drawings, the line 701 shows the position at which the signal intensity becomes the maximum (peak) around the phase encoding of 0. In FIG. 7, (a), which shows the state before the correction, it can be seen that the peaks of signal intensity are shifted from each other.

In Step 610, a correction value is calculated from Hb data at the border in order to eliminate gap of the peaks between the stations. For this purpose, border Hb data s2(i, kx') and s1(i+1, kx') of the adjacent stations m(i) and m(i+1) are extracted. These data are one-dimensional data aligned along the border (Step 611). Then, data (reference data), r2(i, x') and r1(i+1, x'), are obtained by inverse Fourier transform of the extracted one-dimensional data (Step 612). In this case, the one-dimensional data s1 and s2 are aligned in a direction slightly inclined from the kx direction in the kx-z space in which the kx-axis is the vertical axis, and the z-axis is the horizontal axis, and therefore the data are indicated with the variables kx' and x' for axes of inclined directions instead of the variables kx and x. FIG. 8, (a) schematically shows signal intensities of s2(i, kx') and s1(i+1, kx') for the kx' axis, and FIG. 8, (b) and (c) schematically show intensity and phase of s2(i, kx') and s1(i+1, kx') after inverse Fourier transform 801.

Then, linear components p2(i) and p1(i+1) of phase of the reference data r2(i, x') and r1(i+1, x') obtained by inverse Fourier transform of s1 and s2 are calculated (Step 613). The linear components of phase correspond to inclinations of reference data r2(i, x') and r1(i+1, x') shown in FIG. 8, (c), and correction values for coinciding these inclinations with those of the station used as a reference are calculated. Here, the station for which the first measurement is performed is defined as the reference station, i.e., the station m(1), the phase of this reference data, p(1), is defined to be 0, and phase correction values p(i+1) of the stations are calculated as follows (Step 614).

$$p(i+1)=p(i)+p2(i)-p1(i+1)$$

Then, station Hb data are corrected by using the correction value for each station. The correction is completed by changing the linear phase in the x-direction of the x-z space data, which are obtained by inverse Fourier transform of the whole station m(i+1) in the kx-direction, by p(i+1), and then performing Fourier transform of the space data in the x-direction again (Steps 615 and 616). By this operation, m(i+1) is shifted in the kx direction as indicated with an arrow 702 in FIG. 7, (b), thus the gap at the line 701 of the signal peaks around kx=0 is eliminated, and the stations are smoothly connected with regard to intensity at the border. Although the border data used in Steps 611 and 612 may be a single data s2(i, kx'), s1(i+1, kx') for one border, the data may be values obtained by adding data for a width of several pixels (for example, five lines) along the z direction (or −z direction) from the border, or averages of such data. By using such values, influence of noise can be ameliorated, and stable correction results can be obtained.

Then, discontinuity of phase at the border of stations is corrected (Step 620). Border data s2' (i, kx) and s1' (i+1, kx) are extracted again from the station Hb data corrected in Step 610 (611 to 616), and phases q2(i) and q1(i+1) of the points providing maximum absolute values are found (Steps 621 and 622). Then, a correction value that makes phase difference of each station zero is calculated (Step 422). Also in this case, the first station is used for a reference of phase, and a correction value q(i+1) is calculated in accordance with the following equations.

$$q(i+1)=q(i)+q2(i)-q1(i+1)$$

$$q(1)=0$$

The correction is completed by changing the phases of all the stations m(i+1) by q(i+1) (Step 623). By this operation, phase is smoothly connected at the border of the stations as shown in FIG. 9. Finally, inverse Fourier transform of the Hb data of total FOV is carried out in the phase encoding direction to obtain a total image (FIG. 4, Step 404), and it is displayed on the display 110 (FIG. 4, Step 405).

As explained above, according to this embodiment, it becomes possible to smoothly connect gaps of intensity and phase of kx-z space data, and suppress artifacts generated due to inhomogeneity of static magnetic field.

<Second Embodiment>

As the first embodiment, a method of separately performing Step 610 of correction for intensity continuity and Step 620 of correction for phase continuity was explained. In contrast, in this embodiment, both the corrections are performed by one operation. The flow of the second embodiment is shown in FIG. 10. In the drawing, the same operations as those of the first embodiment are indicated with the same numerals, and detailed explanations thereof are omitted.

Also in this embodiment, border Hb data s2($i$, kx') and s1($i$+1, kx') of the adjacent stations m(i) and m(i+1) are extracted, and r2($i$, x') and r1($i$+1, x') are obtained by inverse Fourier transform of the extracted data, like the first embodiment (Steps 611 and 612). However, in this embodiment, when the linear components of phase p1($i$+1) and p2($i$), are obtained from the data r2 and r1, zero-order components thereof (represented as p10($i$+1) and p20($i$), respectively) are also obtained simultaneously, and correction values for coinciding the zero-order components with that of reference in each station are calculated (Steps 631 and 632). The zero-order phase correction values for each station are calculated in accordance with, for example, the following equations.

$$p0(i+1)=p0(i)+p20(i)-p10(i+1),$$

$$p0(1)=0$$

For the correction, in the x-z space data obtained by inverse Fourier transform of the total stations m(i+1) in the kx direction, the zero-order components of the x-direction are changed by p0($i$+1), and linear phases are changed by p(i+1) (Step 633). By performing Fourier transform of these x-z space data in the x-direction again, Hb data corrected for both phase continuity and intensity continuity are obtained.

According to this embodiment, Step 620 of the first embodiment can be omitted, thus the operation is simplified, and therefore operation time can be shortened.

<Third Embodiment>

According to the first and second embodiments, for obtaining linear correction values used for correction of intensity continuity, data r2 and r1 obtained by inverse Fourier transform of border data s2 and s1 are used, and linear components of phases of them are used. In this embodiment, a cross correlation function of data s2($i$, kx') and s1($i$+1, kx') is calculated instead of calculating linear components of phase, and a position at which it becomes the largest is obtained as a correction value. Correction of zero-order components is the same as that of the first or second embodiment.

This cross correlation function R is represented by the following equation.

$$R_{i,i+1}(k) = \frac{1}{N_x - |k|} \sum_{k'_x = -N_x/2}^{N_x/2-1} s2(i, k'_x + k) s1(i+1, k'_x)$$ [Equation 1]

(in the equation, Nx represents number of data points in the kx direction)

The value of k ($-N_x/2 \leq k \leq N_x/2-1$) providing the maximum value of this function $R_{i,j+1}(k)$ is calculated, and used as the shift amount.

The correction is completed by shifting Hb data of the total stations m(i+1) by the calculated shift amount in the kx direction. Further, zero-order components are corrected in the same manner as that of the first or second embodiment. Inverse Fourier transform of the corrected Hb data of total FOV is performed in the kx direction to obtain image data of total FOV, like the other embodiments.

In this embodiment, the operation of obtaining the cross correlation function is needed, but the step of performing inverse Fourier transform of the border data s2 and s1 to obtain reference data r2 and r1 used in the first embodiment is unnecessary. Moreover, according to this embodiment, the shift amount can be calculated with better accuracy compared with the first or second embodiment, where the linear components of phase are used, even when the signal to noise ratio (S/N) of shape or data of imaging object is low.

<Fourth Embodiment>

In the second embodiment, only the zero-order components and linear components of phase are corrected. However, terms of still higher order may also be corrected. By also correcting a term of still higher order, correction for continuity of intensity and phase can be performed with better accuracy. For this embodiment, a case of correcting terms of up to n-th order (n is an integer) is explained below. The flow of the fourth embodiment is shown in FIG. 11. In the drawing, the same operations as those of the first embodiment are indicated with the same numerals, and detailed explanations thereof are omitted.

Also in this embodiment, border Hb data s2($i$, kx') and s1($i$+1, kx') of the adjacent stations m(i) and m(i+1) are extracted, and r2($i$, x') and r1($i$+1, x') are obtained by inverse Fourier transform of the extracted data at the beginning of the correction step 630, like the first embodiment (Steps 611 and 612). However, in this embodiment, phase differential of the both, r21=arctan(r2/r1), is calculated (Step 641). By calculating r2/r1 and then calculating arctan thereof as described above, r21 can be directly calculated without calculating phases of r2 and r1, respectively. Namely, if r1 and r2 are defined as $$r1 = ae^{j\theta_a}, \quad r2 = be^{j\theta_b}$$ [Equation 2]

r2/r1 and r21 are represented as follows.

$$r2/r1 = be^{j\theta_b} / ae^{j\theta_a}$$ [Equation 3]
$$= b/a e^{j(\theta_b - \theta_a)}$$
$$r21 = \arctan(r2/r1)$$
$$= \theta_b - \theta_a$$

Then, a polynomial of n-th order (n is an integer), f(i+1, x'), is obtained by fitting based on the least square method or the like using r21, and a correction value p is calculated as follows (Step 642).

$$p(i+1,x')=p(i,x')-f(i+1,x'), p(1,x')=0$$

Since the phase differential r21 of r2 and r1 is directly obtained, aliasing of phase becomes unlikely to occur, and thus precision or stability at the time of obtaining the components by fitting can be made higher. The reason why aliasing of phase becomes unlikely to occur is that the phase of r21 is the differential of r2 and r1, and therefore change is not so large as that of the phase of r2 or r1.

For the correction, in the x-z space data obtained by inverse Fourier transform of the total stations m(i+1) in the kx direction (Step 616), the phases of the x-direction are changed by p(i+1, x) (Step 643). By performing Fourier transform of these x-z space data in the x-direction again, Hb data corrected for both phase continuity and intensity continuity are obtained.

According to this embodiment, Step 620 of the first embodiment can be omitted, thus the operation is simplified, and therefore operation time can be shortened. Moreover, since the phase differential is directly obtained, precision or stability at the time of obtaining the phase components can be improved. Furthermore, since phase error components of the secondary or still higher order are also corrected, correction accuracy is improved, and artifact-suppressing effect also becomes higher.

Embodiments of the correction operation for station data have been explained above. These correction operations are performed according to a program preliminarily installed in the computer 109 of the MRI apparatus shown in FIG. 1, more precisely, the signal processing part shown in FIG. 3.

Display function of an MRI apparatus provided with the aforementioned correction function will be explained below.

FIG. 12 shows an example of display screen displaying an image obtained by continuous moving table imaging. According to the embodiment shown in the drawing, a mark 1101 which indicates border of stations is displayed at the position of the border.

Even when image reconstruction is performed with correction of discontinuity of stations as described above, artifacts may not be completely suppressed depending on the condition of apparatus distortion at the time of imaging. Depending on the appearing state of artifacts, it becomes difficult to determine whether they indicate pathological change or not. If the reconstructed image 1100 is displayed with such a mark 1101 as shown in FIG. 11 at the border of stations, it becomes relatively easy to determine whether there are artifacts or not. The border of stations inclines from the kx axis, and spreads with respect to the z direction as shown in FIG. 5. However, artifacts are generally generated near the position of the border at which kx is 0, and therefore it is preferable to display the mark 1101 at that position.

EXAMPLE

In order to confirm the effect of the present invention, continuous moving table imaging was performed with the following imaging conditions, and images obtained with and without correction for discontinuity according to the present invention (method of the first embodiment) were compared. As the object of imaging, such an object of imaging having an elliptical shape as shown in FIG. 13, (c) was used.

Imaging conditions: method: GrE method, TR/TE: 14/5 ms, sub FOV: 350 mm, submatrix (matrix size of one station): 128×128, read-out direction: z, phase encoding direction: x, table speed: 0.15 m/s, number of stations: 2

The results are shown in FIGS. 13 and 14. FIG. 13(a) shows an intensity image of data arranged in the kx-z space, and FIG. 13(b) shows a reconstructed image of the results obtained by inverse Fourier transform of the intensity image shown in FIG. 13(a) in the kx direction without the correction. In the kx-z space shown in FIG. 13(a), it can be seen that intensity became discontinuous between stations, and a gap was generated at the position indicated with a white arrow. This gap was generated because the data were substantially linearly distorted in the kx direction in proportion to z in the kx-z space for every station. As a result, in the image of FIG. 13(b), artifacts generated on the upside and downside around the center were observed. These artifacts are considered to be those generated by inhomogeneity of static magnetic field, which was generated because correction for discontinuity was not performed.

FIG. 14 shows the results obtained from the same data as those used for FIG. 13(a) with correction of the data. FIG. 14(a) shows an intensity image of the kx-z space data, and FIG. 14(b) shows a reconstructed image. As shown in FIG. 14(a), it can be confirmed that the gap at the border of stations was eliminated by the correction operation, and thus the stations were smoothly connected concerning intensity. Moreover, although not shown in the drawing, phase was also smoothly connected as a result of the correction operation. Therefore, artifacts observed in FIG. 13(b) were not generated in the reconstructed image of FIG. 14(b).

INDUSTRIAL APPLICABILITY

According to the present invention, an image in which artifacts generated due to inhomogeneity of static magnetic field are suppressed can be obtained in the continuous moving table imaging, in which it is difficult to eliminate influence of inhomogeneity of static magnetic field. Moreover, since the correction for suppressing artifacts does not require acquisition of the static magnetic field inhomogeneity data, which takes time, or the like, the effectiveness of the continuous moving table imaging providing favorable time efficiency can be maintained. Clinical application of the continuous moving table imaging thus becomes possible.

DESCRIPTION OF NUMERICAL NOTATIONS

Figure 1:
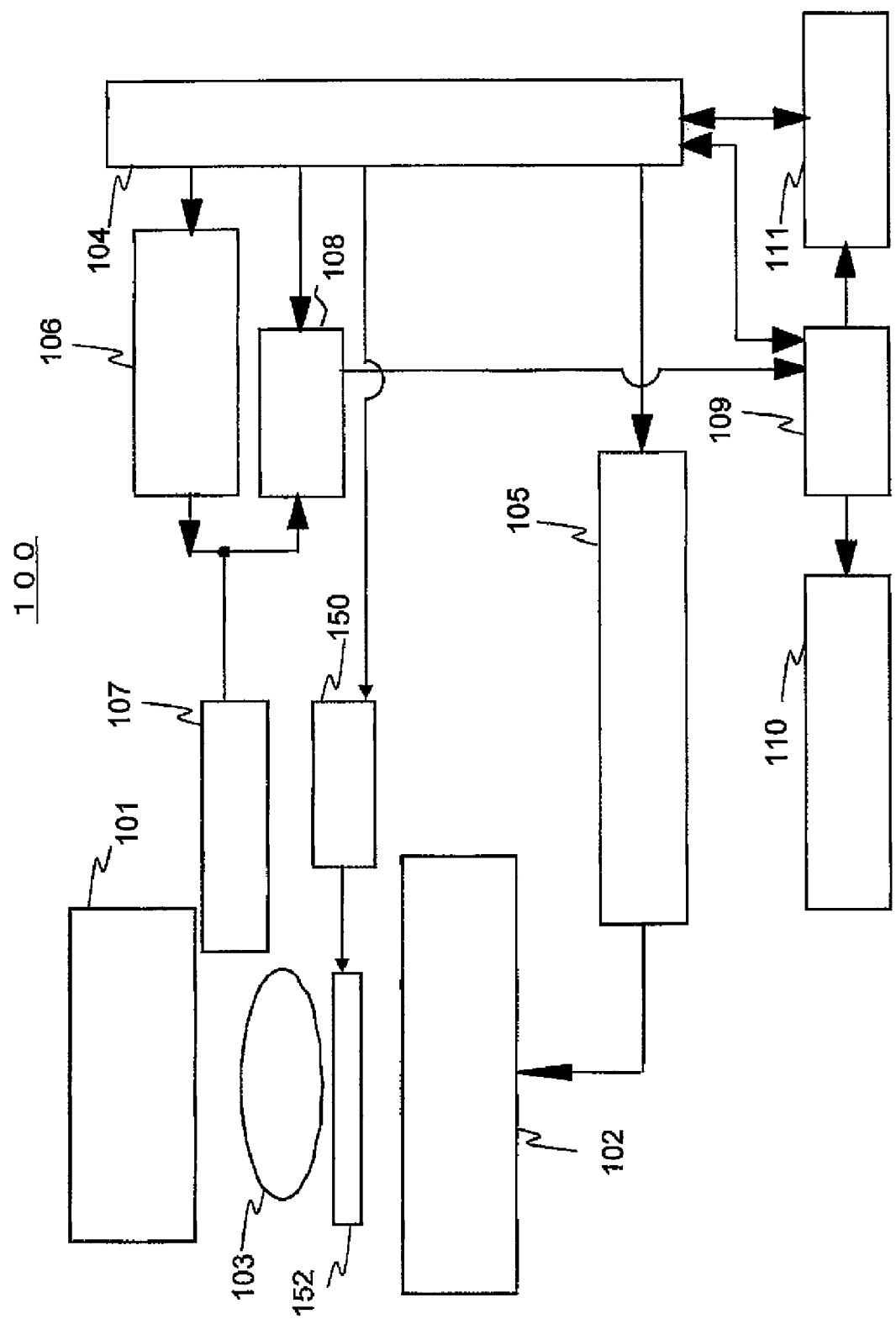
[FIG. 1] A block diagram of an MRI apparatus to which the present invention is applied
Figure 2:
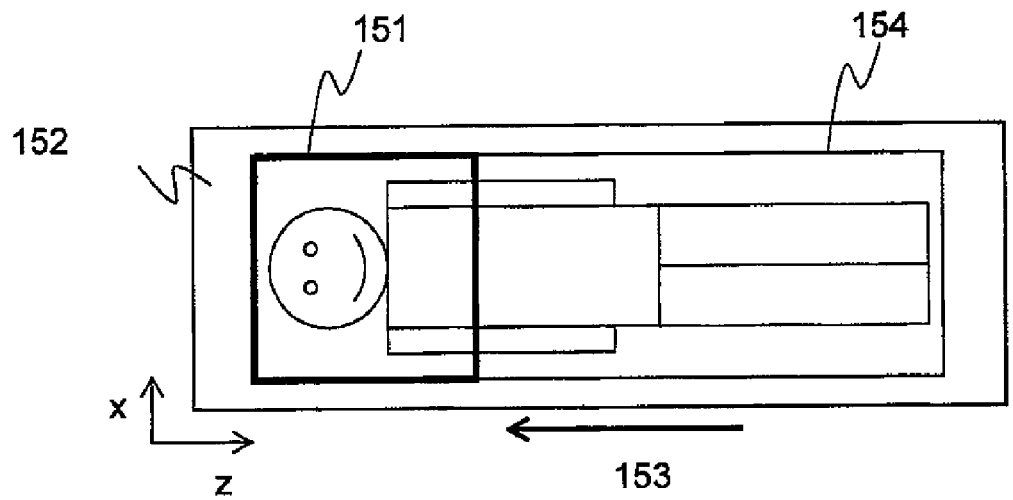
[FIG. 2] A drawing for explaining the relation between table and imaging field of view
Figure 3:
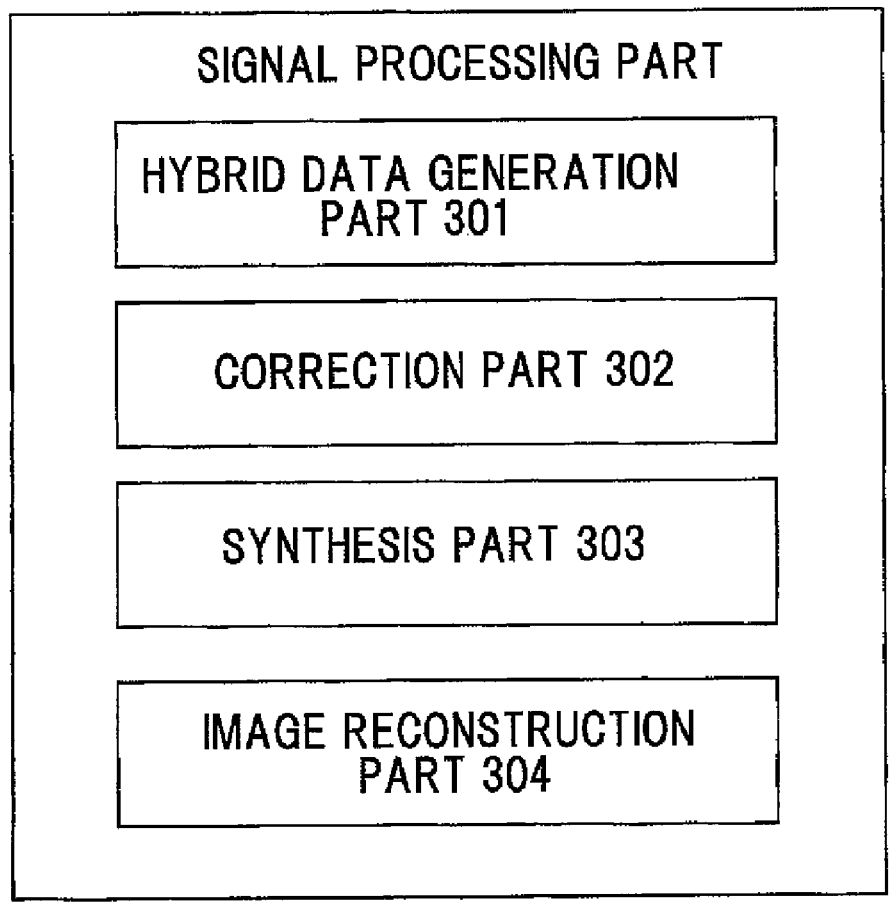
[FIG. 3] A drawing showing detailed configuration of signal processing part
Figure 4:
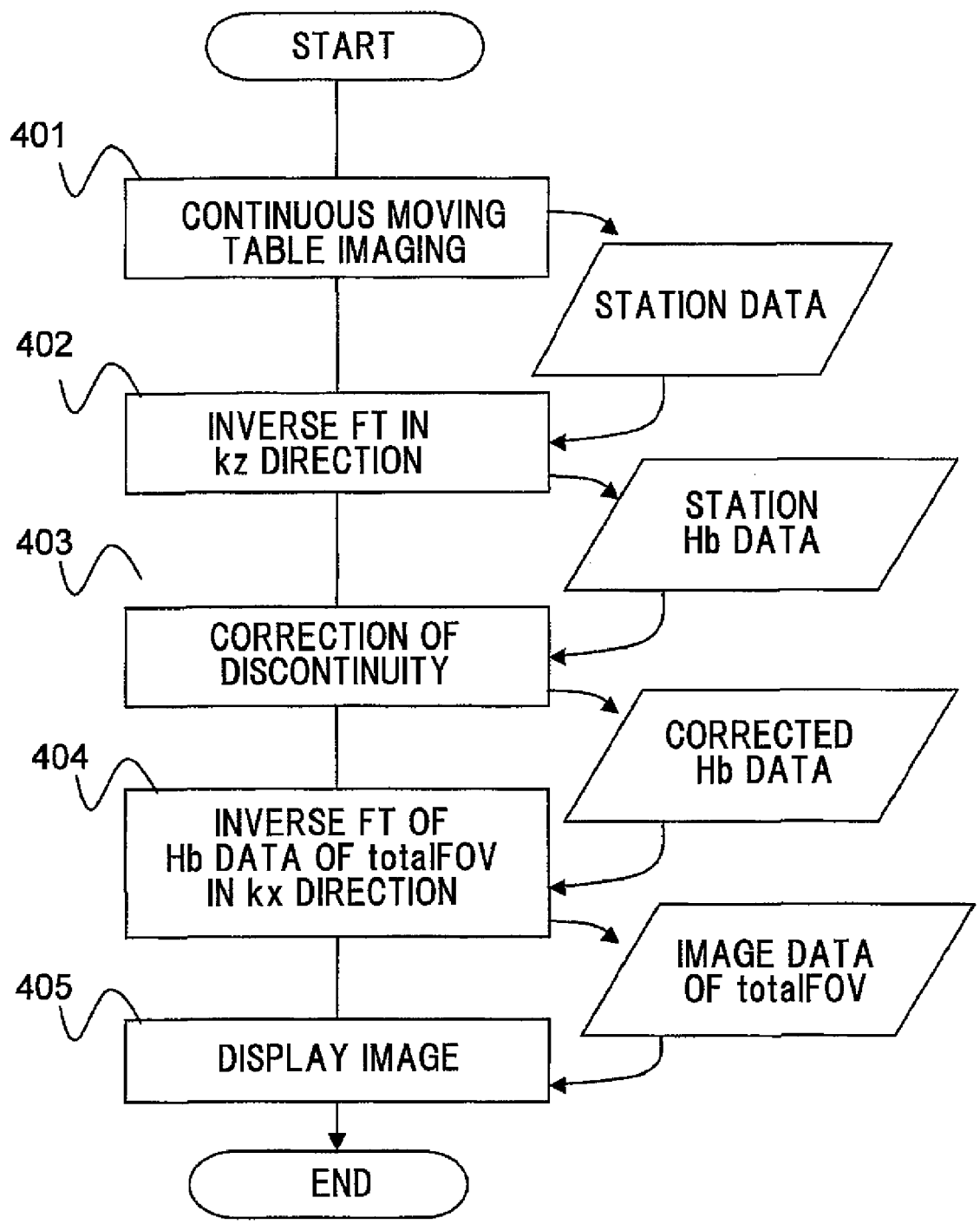
[FIG. 4] A flowchart showing an embodiment of imaging by the MRI apparatus of the present invention
Figure 5:
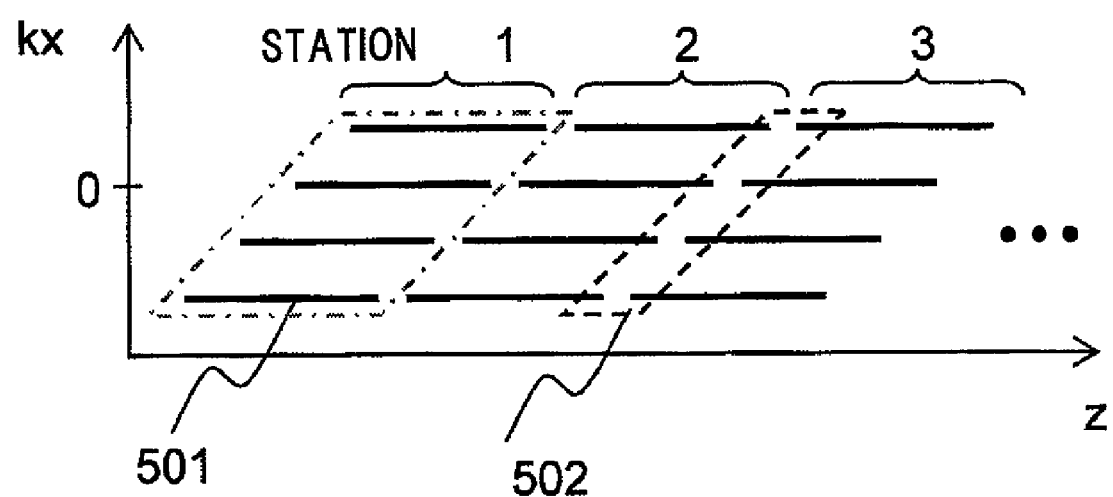
[FIG. 5] A drawing showing hybrid data sets obtained by continuous moving table imaging
Figure 6:
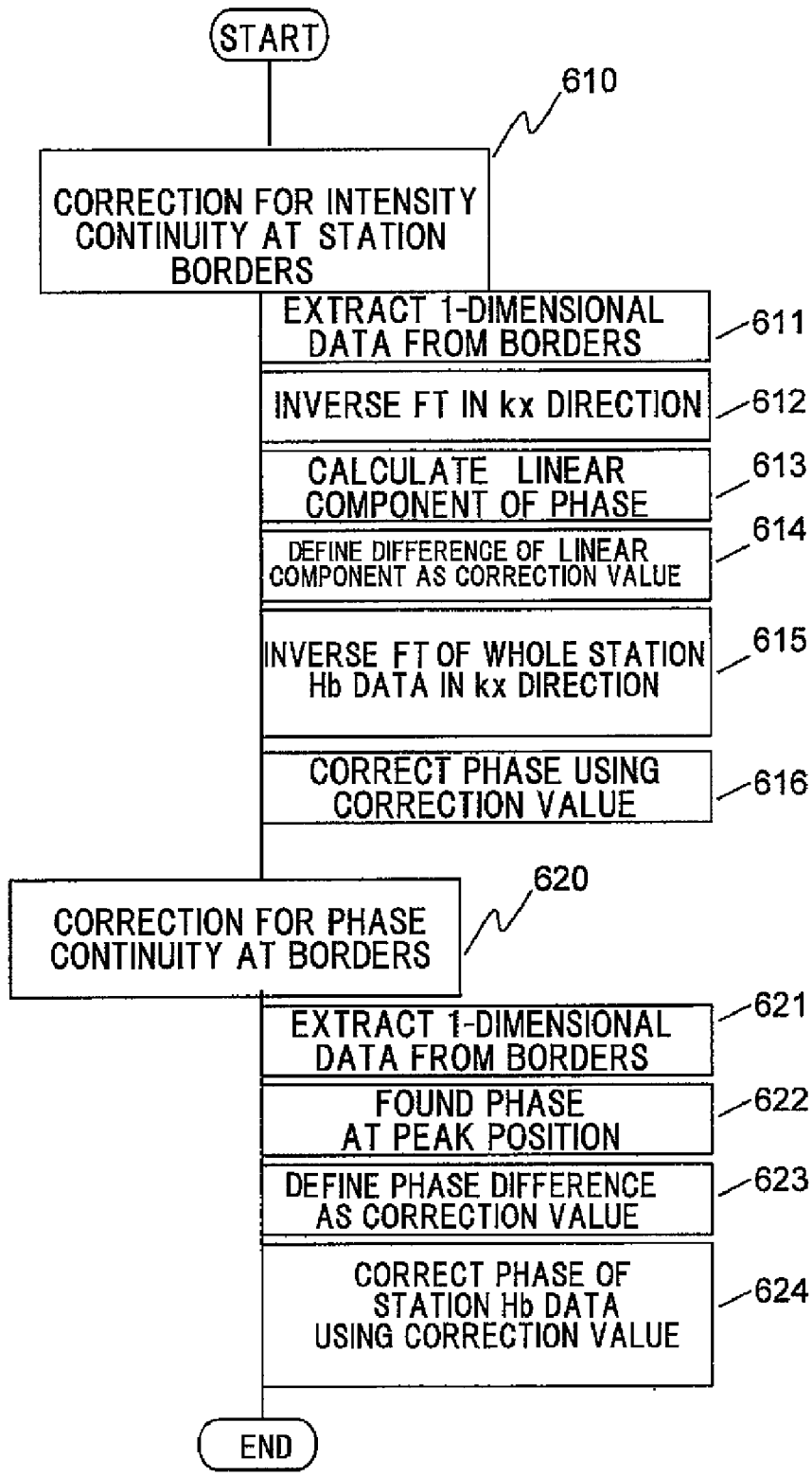
[FIG. 6] A flowchart of correction operation of the first embodiment
Figure 7:
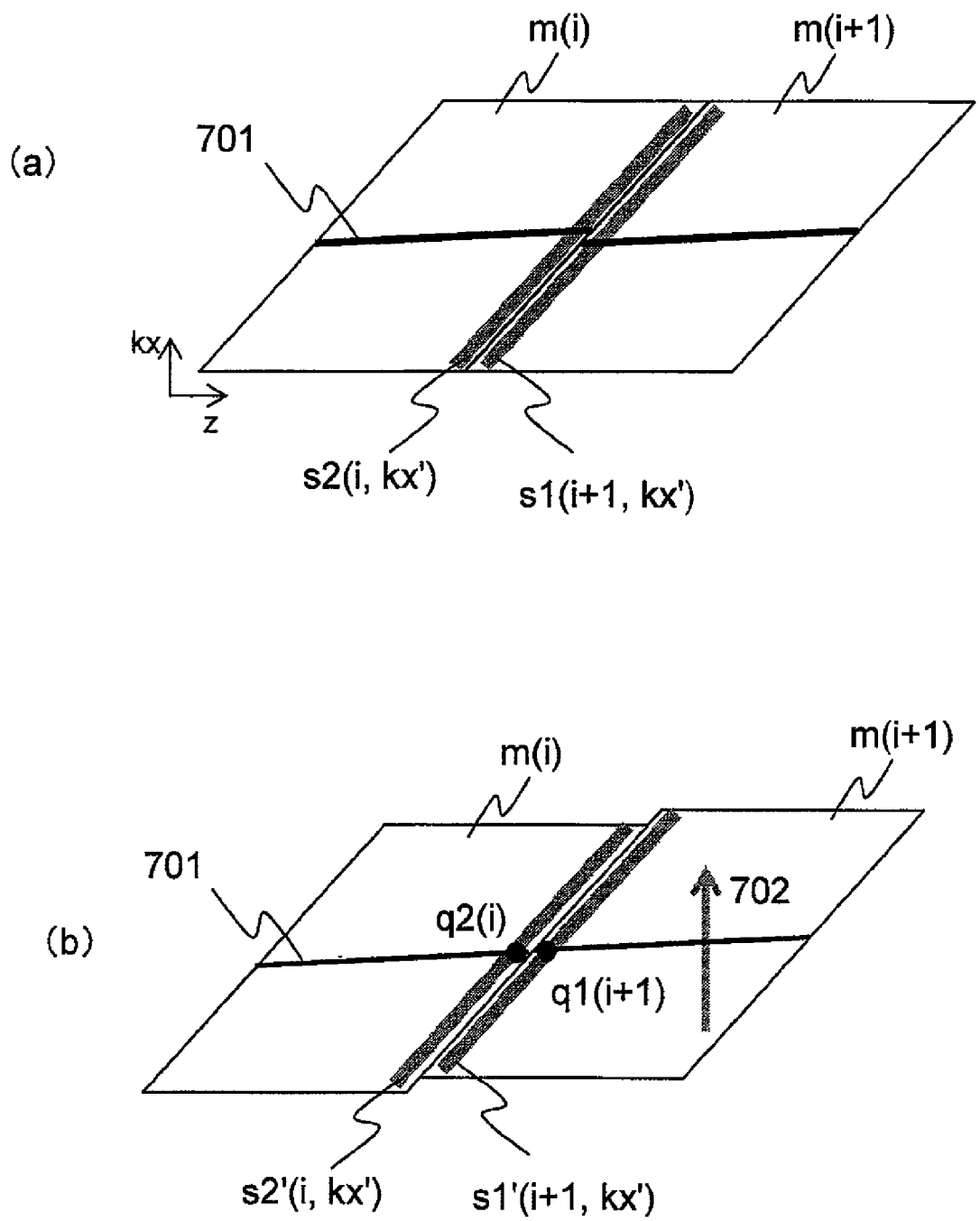
[FIG. 7] Drawings for explaining correction for intensity continuity of the first embodiment
Figure 8:
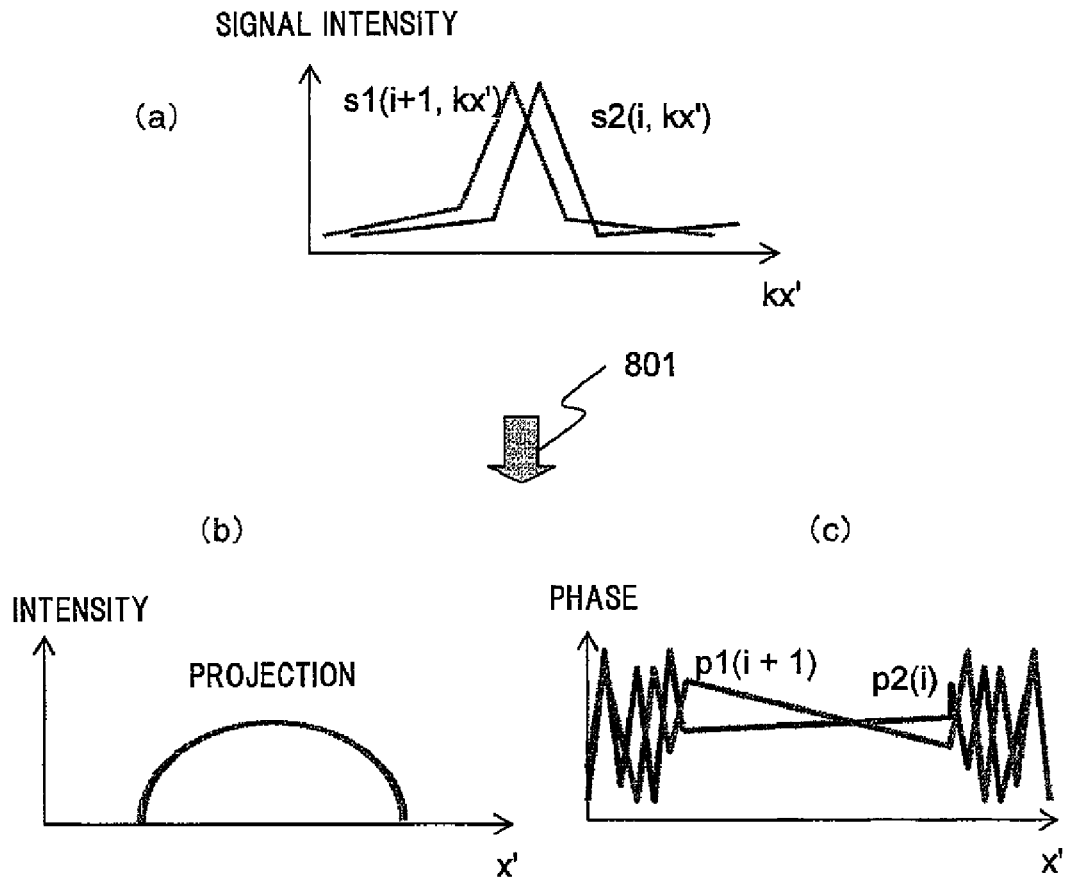
[FIG. 8] Drawings for explaining correction for intensity continuity and correction for phase of the first embodiment
Figure 9:
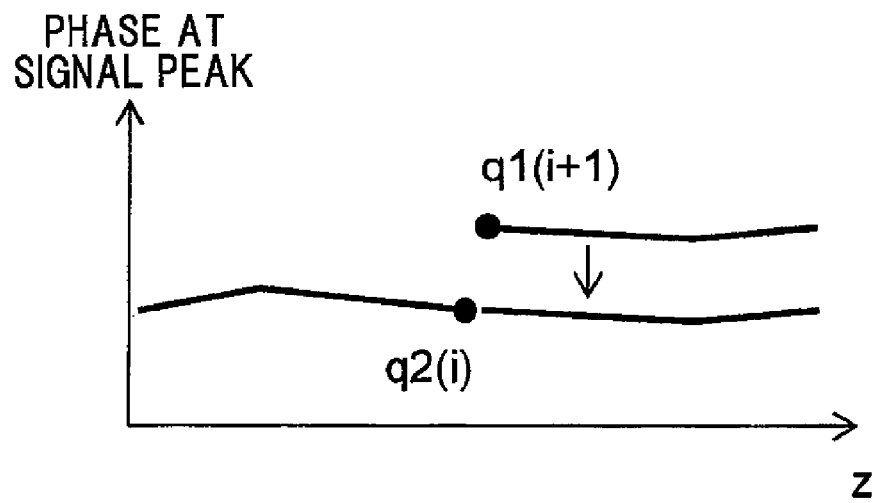
[FIG. 9] A drawing for explaining phase correction of the first embodiment
Figure 10:
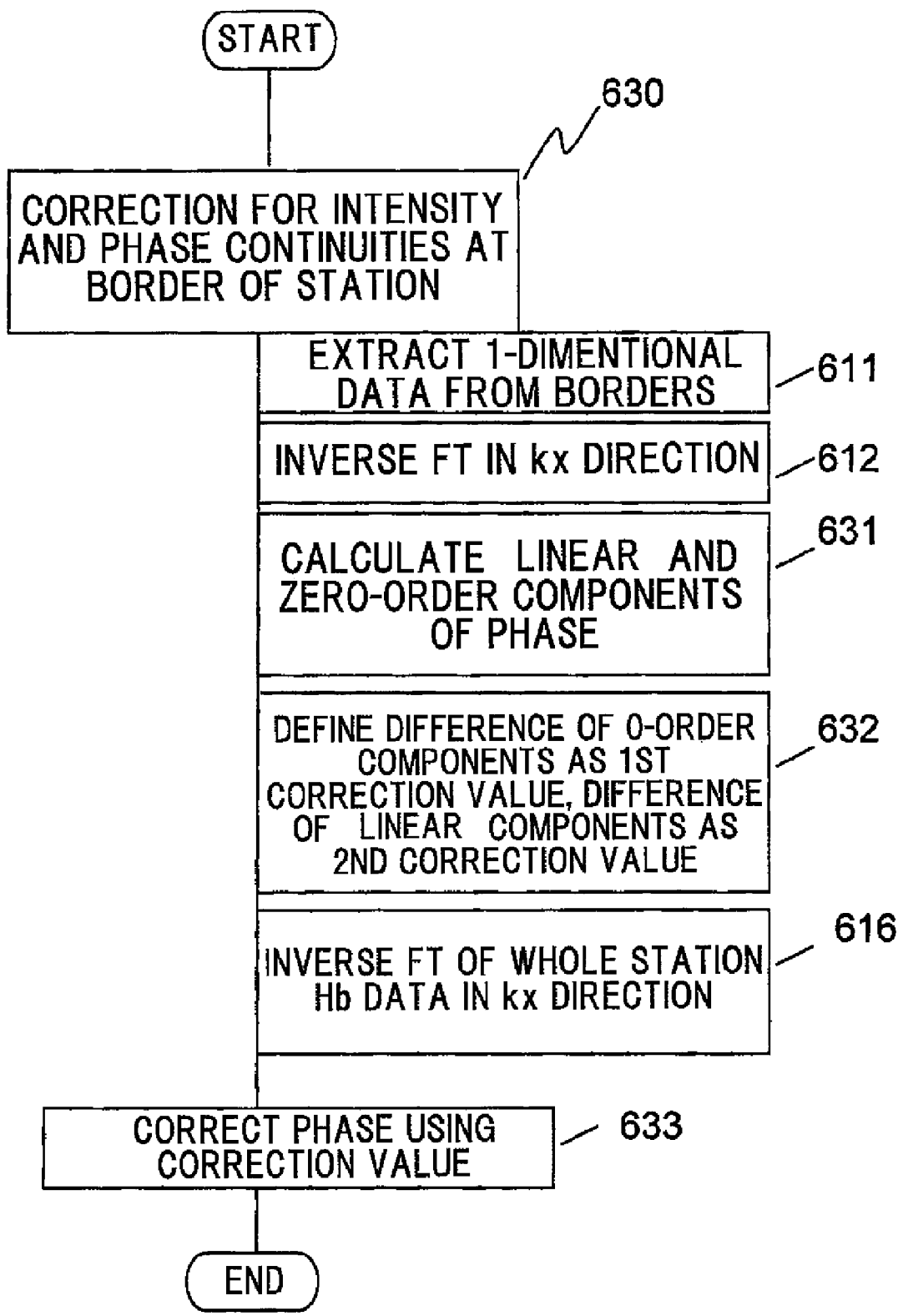
[FIG. 10] A flowchart of correction operation of the second embodiment
Figure 11:
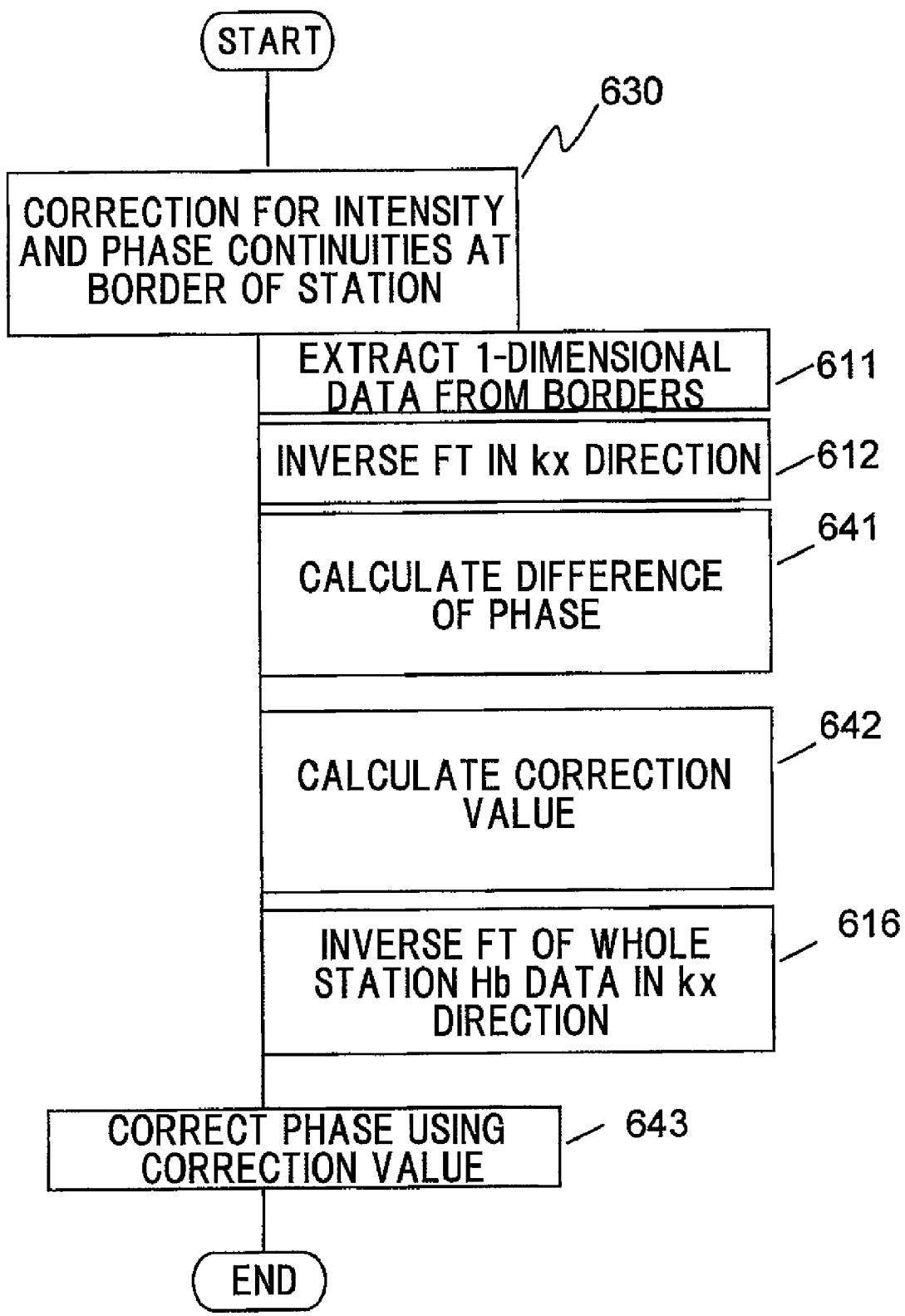
[FIG. 11] A flowchart of correction operation of the fourth embodiment
Figure 12:
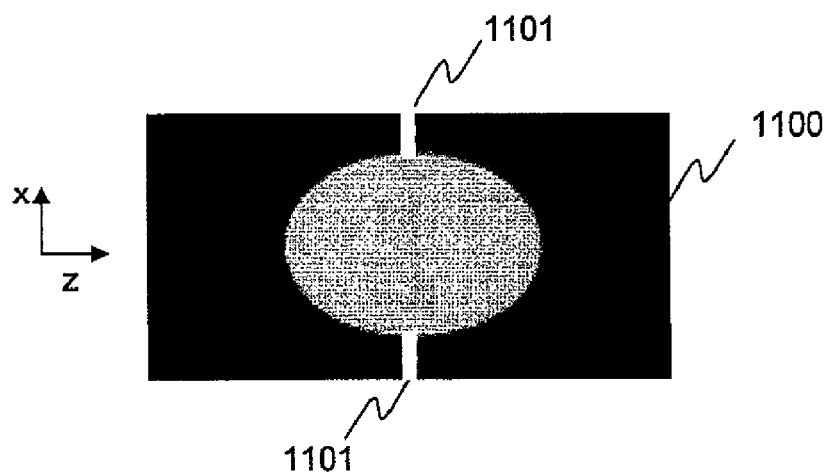
[FIG. 12] A drawing showing an example of displayed image reconstructed by the MRI apparatus of the present invention
Figure 13:
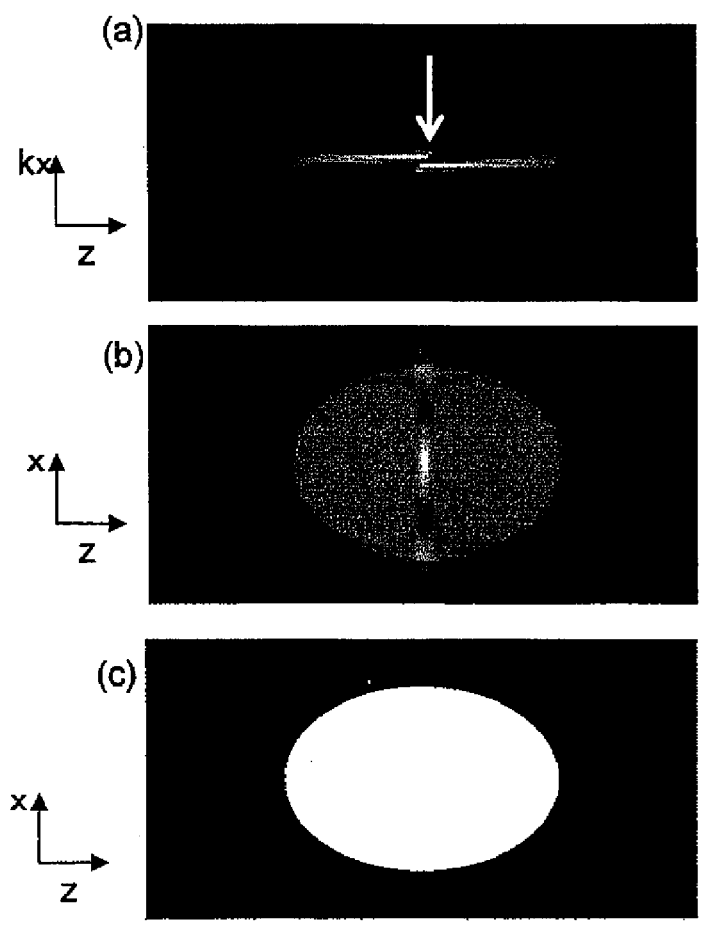
[FIG. 13] Drawings showing intensity image and reconstructed image obtained without performing correction operation
Figure 14:
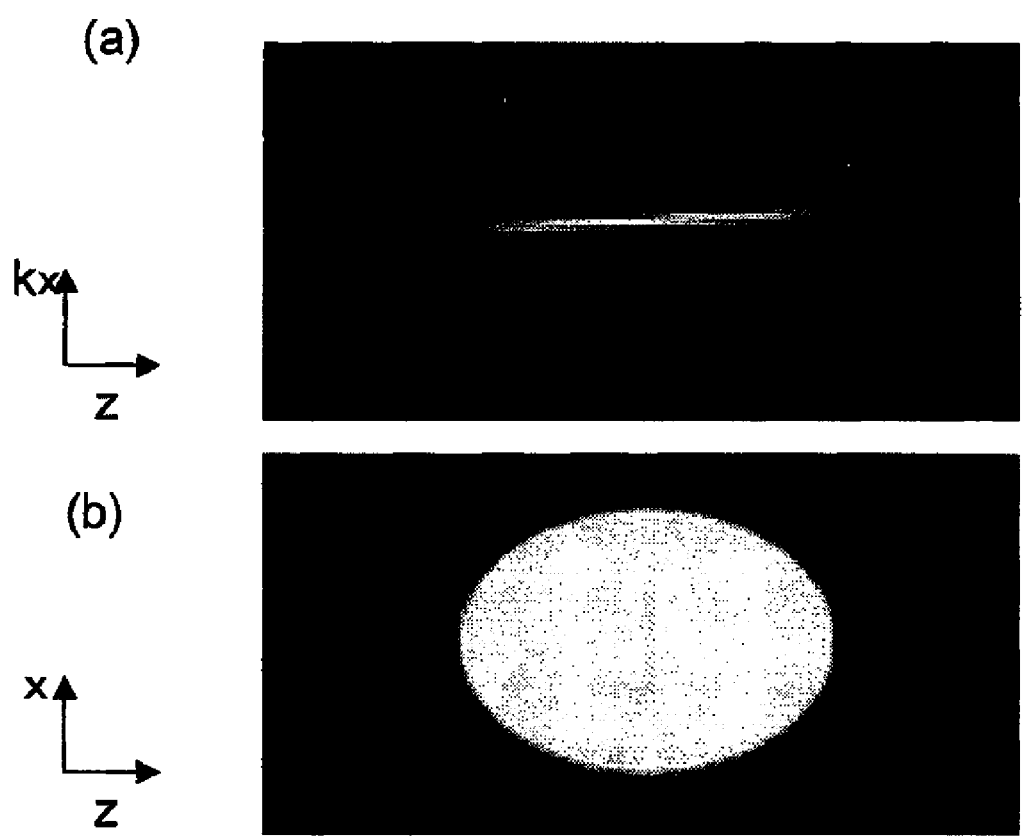
[FIG. 14] Drawings showing intensity image and reconstructed image obtained with performing correction operation

100: MRI apparatus, 101: magnet which generates static magnetic field, 102: gradient coil, 103: subject, 104:

sequencer, 105: gradient magnetic field power supply, 106: radio frequency magnetic field generator, 107: probe, 108: receiver, 109: computer, 110: display, 111: storage medium, 150: table movement control part, 151: sub field of view, 152: table, 153: direction of table movement, 154: imaging area, 301: hybrid data generation part, 302: correction part, 303: synthesis part, 304: image reconstruction part.

The invention claimed is:

1. A magnetic resonance imaging apparatus comprising a table on which a subject is placed, a static magnetic field application part which applies a static magnetic field to the subject, a gradient magnetic field application part which applies a gradient magnetic field to the subject, an RF signal transmission and reception part which transmits and receives RF signals to and from the subject, a table driving part which moves the table relatively to the static magnetic field application part, a data processing part which creates image data from RF signals received by the RF signal transmission and reception part, and a control part which controls operations of the gradient magnetic field application part, the RF signal transmission and reception part, and the table driving part, wherein:

the control part controls the parts so that an operation of applying the gradient magnetic field to perform one cycle of phase encoding of a predetermined range while the table is relatively moved by the table driving part and thereby obtain a data set consisting of multiple RF signals should be repeated multiple times, and the data processing part comprises a hybrid data generation part which performs one-dimensional inverse Fourier transform of the data set obtained in each of the operations of multiple times in the read-out direction and thereby converts it into a hybrid data set, a correction part which performs correction for signal intensity continuity and phase continuity at borders of the multiple hybrid data sets generated by the hybrid data generation part, and an image generation part which synthesize the hybrid data corrected by the correcting part and then performs one-dimensional inverse Fourier transform of the data in the direction of phase encoding.

2. The magnetic resonance imaging apparatus according to claim 1, wherein:

the correction part extracts one-dimensional data from the hybrid data set at a border region with respect to an adjacent hybrid data set, and calculates a correction value used for the correction operation from the one-dimensional data.

3. The magnetic resonance imaging apparatus according to claim 2, wherein:

the correction part uses a difference of linear components of phases of reference data obtained by one-dimensional inverse Fourier transform of one-dimensional data extracted from each hybrid data set at a border region with respect to the adjacent hybrid data set as a correction value in the correction of the adjacent hybrid data sets, obtains real space data by performing inverse Fourier transform of one of the hybrid data sets in the direction of phase encoding, and then corrects linear components of phase in the phase encoding direction of the real space data by the correction value.

4. The magnetic resonance imaging apparatus according to claim 3, wherein:

the correction part performs Fourier transform of the real space data corrected with the correction value again to return them to a hybrid data set, extracts one-dimensional data from the hybrid data set after the Fourier transform at a border region with respect to the adjacent hybrid data set, calculates difference of phase at the maximum signal value of the one-dimensional data, and corrects phase of one of the adjacent hybrid data sets by the difference of phase.

5. The magnetic resonance imaging apparatus according to claim 2, wherein:

in the correction of the adjacent hybrid data sets, the correction part calculates a cross correlation coefficient of the one-dimensional data extracted from each of the hybrid data sets, and shifts one of the hybrid data sets to the position where the cross correlation coefficient takes the maximum value in the phase encoding direction.

6. The magnetic resonance imaging apparatus according to claim 2, wherein:

in the correction of the adjacent hybrid data sets, the correction part calculates a first correction value used for correction for phase continuity and a second correction value used for correction for intensity continuity by using the one-dimensional data extracted from each of the hybrid data sets.

7. The magnetic resonance imaging apparatus according to claim 6, wherein:

the correction part uses difference of zero-order components of phase of reference data obtained by performing one-dimensional inverse Fourier transform of the one-dimensional data as the first correction value, and difference of the linear components of the reference data as the second correction value, obtains real space data by carrying out inverse Fourier transform of one hybrid data set of the adjacent hybrid data sets in the direction of phase encoding, and then corrects zero-order components of phase of the phase encoding direction of the real space data by the first correction value and the linear components by the second correction value.

8. The magnetic resonance imaging apparatus according to claim 2, wherein:

the correction part adds multiple one-dimensional data around a border region at the time of extracting the one-dimensional data.

9. The magnetic resonance imaging apparatus according to claim 1, wherein:

the correction part uses one hybrid data set among multiple hybrid data sets as a reference, and corrects the other hybrid data sets with respect to the reference.

10. The magnetic resonance imaging apparatus according to claim 1, wherein:

the data processing part comprises a display part which displays image data generated by the image generation part together with an indication of a position on the image corresponding to a border of adjacent hybrid data sets.

11. The magnetic resonance imaging apparatus according to claim 2, wherein:

in the correction of the adjacent hybrid data sets, the correction part obtains reference data by performing one-dimensional inverse Fourier transform of the one-dimensional data extracted from the border region of each hybrid data set, obtains an n-th polynomial from phase difference of the reference data by fitting, obtains real space data by performing inverse Fourier transform of one of the hybrid data sets in the direction of phase encoding, and corrects phase of real space data in the direction of phase encoding by a phase value obtained from the polynomial.

* * * * *